United States Patent [19]
Chornenky et al.

[11] Patent Number: 6,069,938
[45] Date of Patent: May 30, 2000

[54] METHOD AND X-RAY DEVICE USING PULSE HIGH VOLTAGE SOURCE

[76] Inventors: Victor Ivan Chornenky, 5524 Mayview Rd., Minnetonka, Minn. 55345; Dale Loren Schreiner, 9380 Country Rd. 140, Cologne, Minn. 55322; Graham Steven Kerslick, 1520 E. Minnehaha Pkwy., Minneapolis, Minn. 55417; Michael Roy Satteson, 972 McLean Ave., St. Paul, Minn. 55106; Ali Jaafar, 8077 Starting Gate La., Cincinnati, Ohio 45249

[21] Appl. No.: 09/067,844

[22] Filed: Apr. 27, 1998

[51] Int. Cl.⁷ ..................................................... H01J 35/32
[52] U.S. Cl. ................................................ 378/122; 378/65
[58] Field of Search ............................... 378/65, 122, 109, 378/111

[56] References Cited

U.S. PATENT DOCUMENTS

| | | |
|---|---|---|
| Re. 34,421 | 10/1993 | Parker et al. . |
| 1,786,373 | 12/1930 | Walker . |
| 1,881,448 | 10/1932 | Forde et al. . |
| 2,467,812 | 4/1949 | Clapp . |
| 2,766,385 | 10/1956 | Herrnring et al. . |
| 3,005,096 | 10/1961 | Chynoweth . |
| 3,073,960 | 1/1963 | Guentner et al. . |
| 3,125,679 | 3/1964 | Ohde et al. . |
| 3,256,439 | 6/1966 | Dyke et al. . |
| 3,348,051 | 10/1967 | Weighart et al. . |
| 3,381,129 | 4/1968 | Duftschmid . |
| 3,388,314 | 6/1968 | Gould . |
| 3,484,721 | 12/1969 | Bond et al. . |
| 3,508,059 | 4/1970 | Vanderpool . |
| 3,538,919 | 11/1970 | Meyer . |
| 3,564,251 | 2/1971 | Youmans . |
| 3,617,939 | 11/1971 | Bond et al. . |
| 3,628,021 | 12/1971 | MacDonald . |
| 3,691,417 | 9/1972 | Gralenski . |
| 3,714,486 | 1/1973 | McCrary . |
| 3,752,990 | 8/1973 | Fischer . |
| 3,866,050 | 2/1975 | Whitfield . |
| 3,878,394 | 4/1975 | Golden . |

(List continued on next page.)

FOREIGN PATENT DOCUMENTS

| | | |
|---|---|---|
| 2054738 | 5/1972 | Germany . |
| 26 08 418 | 9/1977 | Germany . |
| 58-145098 | 8/1983 | Japan . |
| 814331 | 3/1981 | Russian Federation . |
| WO 95/20241 | 7/1995 | WIPO . |
| WO 96/02059 | 1/1996 | WIPO . |

OTHER PUBLICATIONS

PCT International Search Report (English Translation Abstract of PCT/US96/13629 included) (4 pages).
Brochure: "Dunlee DL–1 Stationary Anode Insert", Dunlee Corporation, Bellwood, IL 60104, Jun. 1972.
Wiedermann, et al., "Effects of high–dose intracoronary irradiationon vasomotor function and smooth muscle histopathology", pp. H125–H132 (1994).

*Primary Examiner*—David P. Porta
*Assistant Examiner*—Drew A. Dunn

[57] ABSTRACT

An apparatus and method for exposing a treatment site in a patient to x-ray radiation is described that uses a pulse voltage source, where the x-ray emitter employs a cold cathode. The invention may further include a current sensor for measuring a current through the x-ray emitter, and, optionally, a current integrator connected to the current sensor. Each voltage pulse may be discontinued when a predetermined amount of charge has passed through the emitter. The step of moving an x-ray emitter past a treatment area at a rate determined by the amount of charge that has passed through the emitter is also described. The present invention also includes an x-ray emitter device with rectangular voltage pulses added to a base direct current voltage. Another step of the invention may be applying a voltage pulse cycle to the x-ray emitter where a duration of the pulse is 2–5 times lower than a thermal relaxation time of an emitter.

16 Claims, 2 Drawing Sheets

6,069,938
Page 2

U.S. PATENT DOCUMENTS

| | | |
|---|---|---|
| 3,883,760 | 5/1975 | Cunningham, Jr. . |
| 3,920,999 | 11/1975 | Drexler et al. . |
| 3,970,884 | 7/1976 | Golden . |
| 3,987,281 | 10/1976 | Hodes . |
| 4,058,486 | 11/1977 | Mallozzi et al. . |
| 4,060,731 | 11/1977 | Rissi . |
| 4,097,759 | 6/1978 | Furbee et al. . |
| 4,104,526 | 8/1978 | Albert . |
| 4,104,530 | 8/1978 | Weiss . |
| 4,104,531 | 8/1978 | Weiss . |
| 4,104,532 | 8/1978 | Weiss . |
| 4,109,154 | 8/1978 | Taumann . |
| 4,117,334 | 9/1978 | Strauts . |
| 4,143,275 | 3/1979 | Mallozzi et al. . |
| 4,158,138 | 6/1979 | Hellstrom . |
| 4,163,901 | 8/1979 | Azam et al. . |
| 4,191,193 | 3/1980 | Seo . |
| 4,344,181 | 8/1982 | Baecklund . |
| 4,359,660 | 11/1982 | Smith et al. . |
| 4,368,538 | 1/1983 | McCorkle . |
| 4,563,769 | 1/1986 | Madsen . |
| 4,607,380 | 8/1986 | Oliver . |
| 4,636,195 | 1/1987 | Wolinksy . |
| 4,646,338 | 2/1987 | Skillicorn . |
| 4,669,467 | 6/1987 | Willett et al. . |
| 4,670,894 | 6/1987 | Birnbach et al. . |
| 4,694,480 | 9/1987 | Skillicorn . |
| 4,701,941 | 10/1987 | Szirmai et al. . |
| 4,702,228 | 10/1987 | Russell, Jr. et al. . |
| 4,715,054 | 12/1987 | Kato et al. . |
| 4,763,671 | 8/1988 | Goffinet . |
| 4,789,997 | 12/1988 | Madsen et al. . |
| 4,794,931 | 1/1989 | Yock . |
| 4,800,581 | 1/1989 | Kujirai et al. . |
| 4,824,436 | 4/1989 | Wolinsky . |
| 4,856,036 | 8/1989 | Malcolm et al. . |
| 4,913,142 | 4/1990 | Kittrell et al. . |
| 4,924,485 | 5/1990 | Hoeberling . |
| 4,966,596 | 10/1990 | Kuntz et al. . |
| 4,976,266 | 12/1990 | Huffman et al. . |
| 4,979,199 | 12/1990 | Cueman et al. . |
| 5,042,486 | 8/1991 | Pfeiler et al. . |
| 5,059,166 | 10/1991 | Fischell et al. . |
| 5,077,771 | 12/1991 | Skillicorn et al. . |
| 5,087,244 | 2/1992 | Wolinsky et al. . |
| 5,090,043 | 2/1992 | Parker et al. ............................ 378/122 |
| 5,099,845 | 3/1992 | Besz et al. . |
| 5,101,422 | 3/1992 | Thiel et al. . |
| 5,106,360 | 4/1992 | Ishiwara et al. . |
| 5,148,463 | 9/1992 | Woodruff et al. . |
| 5,153,900 | 10/1992 | Nomikos et al. . |
| 5,165,093 | 11/1992 | Miller et al. . |
| 5,199,939 | 4/1993 | Dake et al. . |
| 5,222,116 | 6/1993 | Eloff et al. . |
| 5,228,176 | 7/1993 | Bui et al. . |
| 5,264,801 | 11/1993 | Decou, Jr. et al. . |
| 5,290,275 | 3/1994 | Kittrell et al. . |
| 5,313,949 | 5/1994 | Yock . |
| 5,313,950 | 5/1994 | Ishikawa et al. . |
| 5,364,336 | 11/1994 | Carr . |
| 5,369,679 | 11/1994 | Sliski et al. . |
| 5,402,790 | 4/1995 | Jang et al. . |
| 5,414,748 | 5/1995 | Upadhya . |
| 5,422,926 | 6/1995 | Smith et al. . |
| 5,425,735 | 6/1995 | Rosen et al. . |
| 5,428,658 | 6/1995 | Oettinger et al. . |
| 5,437,277 | 8/1995 | Dumoulin et al. . |
| 5,442,678 | 8/1995 | Dinsmore et al. . |
| 5,444,254 | 8/1995 | Thomson . |
| 5,452,720 | 9/1995 | Smith et al. . |
| 5,453,575 | 9/1995 | O'Donnell et al. . |
| 5,454,809 | 10/1995 | Janssen . |
| 5,465,732 | 11/1995 | Abele . |
| 5,469,490 | 11/1995 | Golden et al. . |
| 5,474,075 | 12/1995 | Goldberg et al. . |
| 5,503,613 | 4/1996 | Weinberger . |
| 5,504,799 | 4/1996 | Suzuki . |
| 5,511,107 | 4/1996 | Sliski . |
| 5,528,652 | 6/1996 | Smith et al. . |
| 5,566,221 | 10/1996 | Smith et al. . |
| 5,621,780 | 4/1997 | Smith et al. . |
| 5,623,139 | 4/1997 | Sliski . |
| 5,635,709 | 6/1997 | Sliski et al. . |
| 5,729,583 | 3/1998 | Tang et al. ............................. 378/122 |

METHOD AND X-RAY DEVICE USING PULSE HIGH VOLTAGE SOURCE

BACKGROUND OF THE INVENTION

The present invention relates to an apparatus and method for exposing a treatment area in a passage inside a patient to x-ray radiation. In particular, the invention relates to a method and apparatus for x-ray treatment supplying voltage pulses to an x-ray emitter.

X-ray emitters for medical uses, components of the emitter, and various delivery systems for positioning such a catheter in a passage inside the body of a patient have been described in other co-pending patent applications, such as patent application Ser. No. 08/701,764, "X-RAY CATHETER", the contents of which are hereby incorporated by reference herein.

X-ray devices include a cathode, an anode, and a housing. An electrode applies a voltage to the cathode to cause electron emission. In many x-ray devices it is common to use a thermionic cathode, or a hot cathode, in which the emission properties depend on the temperature of the cathode surface. A hot cathode has an additional electrode providing a low voltage current for heating the cathode. By raising the temperature of the cathode, the emission properties of the cathode improve and the current at the anode improves.

In thermionic cathodes, the anode current and voltage can be controlled and stabilized independently from each other. For example, the voltage may be varied while the anode current, that is directly related to the power deposited at the anode, is kept constant. An x-ray catheter that can be operated so that the voltage and the anode current are controlled and stabilized independently is useful for medical applications.

In many x-ray devices, a field emission cathode, or a cold cathode, is preferred to a hot cathode. Space limitations in a very small device may eliminate the possibility of a third electrode. The desire to avoid heat generation at the x-ray emitter may also preclude the use of a hot cathode.

In a field emission diode, an independent control of the voltage and the current cannot be obtained as described above. The field emission cathode is powered by a direct current high voltage and the value of the field emission current is directly related to the applied voltage. The I–V characteristic of the diode, defined by the Fowler-Nordheim law, is a very steep exponential function of voltage. That is, with increasing voltage, the current increases exponentially. The electrical power developed at the anode is an even steeper function of voltage.

In some medical applications where the x-ray catheter is used, such as the treatment of cancer, it is necessary to operate the x-ray emitter under different applied voltages depending on the patient and the site to be treated. Generally speaking, x-ray radiation emitted at a higher operating voltage will penetrate deeper in the tissue than does x-ray radiation emitted at a lower operating voltage. Additionally, the radiation dose, proportional to the anode current, and the time of irradiation, must be individually selected for every treatment.

One way of overcoming this problem would be to provide a number of x-ray catheters having different configurations so that they operate at different voltages within the necessary range. To obtain the desired treatment, an emitter of the proper operating voltage would be selected, and the tissue would be irradiated until the desired dose had been delivered. However, this solution is impractical because it requires the production of a number of different x-ray emitters with different anode-cathode characteristics which is not desirable from a manufacturing and cost point of view.

Another issue that arises during use of field emission cathodes is incidental heat generation. If an emitter having a field emission cathode operates at a high current for a long time, its temperature can reach undesired levels.

A voltage source is needed for x-ray devices that provides flexibility in supplying voltage and in current requirements, and provides other advantages. A voltage source that minimizes heat production and other disadvantages of a field emission cathode would also be valuable.

SUMMARY OF THE INVENTION

The present invention relates to an apparatus and method for exposing a treatment area in a patient to x-ray radiation. The method of use of the present invention includes positioning an x-ray emitter having a field emission cathode near the treatment area, where the x-ray emitter is connected to a cable, and supplying voltage pulses from a voltage source to the x-ray emitter through the cable. The apparatus of the present invention includes the x-ray emitter which is positionable in the passage, a cable connected to the x-ray emitter, and a pulse voltage source.

The invention may further include a current sensor for measuring a current through the x-ray emitter, and, optionally, a current integrator connected to the current sensor.

According to the method of use of the invention, the voltage pulse may be discontinued when a predetermine amount of charge has passed through the emitter. The present invention may alternatively include the method of moving an x-ray emitter past a treatment area at a rate determined by the amount of charge that has passed through the emitter. The present invention also includes an x-ray emitter drive with rectangular voltage pulses added to a base direct current voltage.

Another embodiment of the method of the invention may be applying a voltage pulse cycle to the x-ray emitter where a duration of the pulse is 2–5 times lower than a thermal relaxation time of an emitter.

These and various other advantages and features of novelty which characterize the invention are pointed out with particularity in the application. However for a better understanding of the invention its advantages and the objects obtained by its use, reference should be made to the accompanying drawings and descriptive matter, which form a further part hereof, and in which there is illustrated and described preferred embodiments of the invention.

BRIEF DESCRIPTION OF THE DRAWINGS

In the drawings wherein corresponding reference numerals generally indicate corresponding parts throughout several views.

DETAILED DESCRIPTION OF THE INVENTION

The present invention includes a voltage source that supplies voltage pulses, so that an x-ray emitter can be used in a wider range of operating voltages, without restricting the dose delivered to the treatment area, which is proportional to the current through the emitter. The voltage pulse may be cut off when a predetermined amount of electrical charge has passed through the emitter so that each pulse is stabilized with respect to the delivered irradiation. The present invention also includes an x-ray emitter device with rectangular voltage pulses added to a base direct current voltage, so that the required pulses have a smaller amplitude. In another aspect of the invention, high voltage pulses may have a fixed duration and pulse cycle repetition rate, but the catheter movement rate may be based on the amount of charge that has passed through the emitter. The invention also includes a method and device for providing a voltage pulse cycle that allows time for thermal relaxation of the emitter between voltage pulses.

Figure 1:
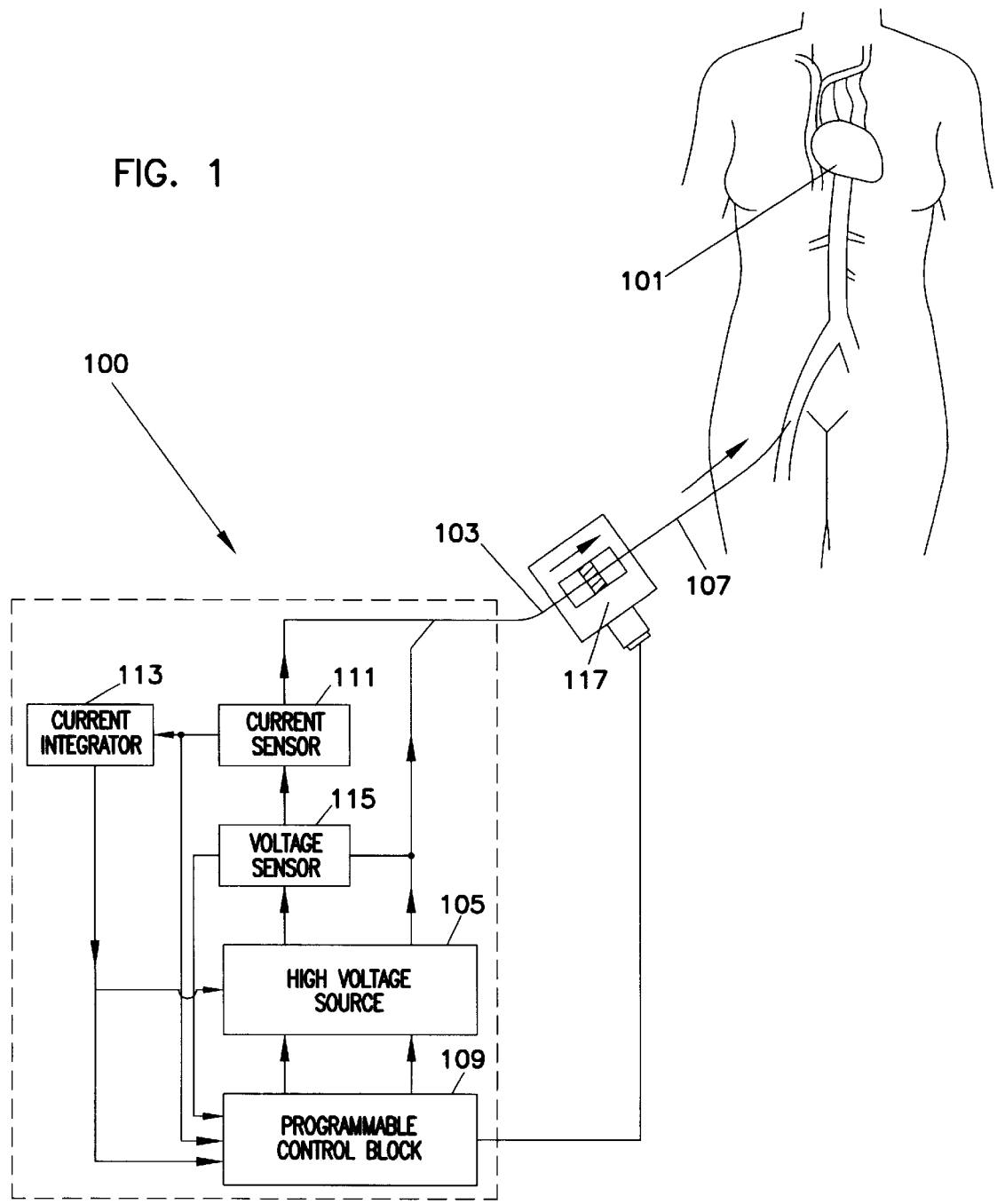
FIG. 1 is a schematic overview of an embodiment of the present invention.

A schematic overview of an embodiment of the apparatus of the invention is shown in FIG. 1. The apparatus 100 comprises an x-ray emitter 101 connected to a cable 103. The x-ray emitter 101 is schematically shown at a position inside a patient's body. The x-ray emitter 101 and cable 103 may be inserted into the patient's body via a suitable blood vessel and advanced through the blood vessel to the desired treatment area. A sheath 107 defines a lumen longitudinally through the sheath, where the x-ray emitter 101 and cable 103 may be situated.

Examples of the x-ray emitter of this application, components of the emitter, and various delivery systems for positioning such a catheter in a passage inside the body of a patient have been described in other co-pending patent applications. The x-ray emitter is described in patent application Ser. No. 08/701,764, "X-RAY CATHETER", the contents of which are incorporated by reference herein. Several delivery devices, systems and methods use with an x-ray emitter are described in U.S. patent application titled "DEVICES, SYSTEMS AND METHODS OF DELIVERING X-RAY RADIATION", filed on Mar. 6, 1998, patent application Ser. No. 09/036,602, the contents of which are hereby incorporated by reference herein.

An x-ray device of the present invention includes an anode and a cathode, arranged within a vacuum housing to produce x-ray radiation. The cathode may include a thin diamond film, and may include a getter material that is activated to improve the quality of the vacuum within the housing, as described in U.S. patent application Ser. No. 08/806,244, which is incorporated by reference herein. The vacuum housing may include a diamond shell, as described in the U.S. patent application titled "HOUSING FOR MINIATURE X-RAY DEVICE", patent application Ser. No. 09/008,202, filed on Jan. 16, 1998, the contents of which are incorporated herein by reference in their entirety. A method and device for using the x-ray emitter with an adaptive high voltage source is described in U.S. Provisional Patent Application "METHOD AND X-RAY DEVICE USING ADAPTABLE POWER SOURCE," filed Mar. 6, 1998, Provisional Patent Application Serial No. 60/077,058, which is incorporated herein by reference in its entirety.

The cable 103 is connected to a pulsed voltage source 105. Different well known pulse voltage sources may be used in the embodiment shown in FIG. 1. The pulse voltage source 105 supplies voltage pulses with a peak voltage ranging from about 15 to 40 KV. Preferably the pulses are periodic, i.e. each pulse cycle, measured from the beginning of one pulse to the beginning of the subsequent pulse, is of equal length in time. Most preferably the pulses are rectangular periodic voltage pulses. Rectangular pulses with a frequency ranging from about 10 to 1000 Hz are suitable for many embodiments. In a first embodiment of the method, the voltage pulse is discontinued when a predetermined amount of charge has passed through the emitter. The specific duration of each voltage pulse is determined by a current sensor 111, so that each pulse delivers a stable dose. Many well-known current sensors can be used with this embodiment. For example, an amperemeter may be used as the current sensor to measure the current through the x-ray emitter.

The current sensor 111 is connected to the cable 103. The current is measured to determine the delivered dose of radiation. The delivered dose is proportional to the amount of current passing through the x-ray emitter, since the emitted amount of radiation is proportional to the current, and since the emitter is typically surrounded by the tissue to be treated. The assumption may be made that all emitted radiation is absorbed by the tissue.

It is expected that the current through the x-ray emitter will have continuous slight variations from a desired value during treatment. Therefore, the delivered dose of radiation during, for example, a 1-minute period cannot be exactly determined without taking into account the momentary current at every instant during the period. By integrating the momentary current values over a time period, an average current during the same time period can be determined, and accordingly, a very accurate measure of the delivered dose may be obtained. To facilitate this, the apparatus 100 may further comprise a current integrator 113 for determining the accumulated charge that has passed through the x-ray emitter 101 during each pulse. Well-known current integrators may be used with the embodiments of this invention. For example, a digital integrator may be used in the embodiment of the invention. The current integrator 113 is connected to current sensor 111, for measuring the momentary values of current as determined by the current sensor 111.

The pulse voltage source 105 may also provide a base direct current voltage to the x-ray emitter 101 through the cable 103. The supplied rectangular voltage pulses may then be added to the base direct current voltage. The base direct current voltage is chosen in consideration of the rectangular voltage pulses to be provided by the pulse voltage source 105. For example the base direct current voltage may range from about 50 to 75 percent of the peak of the rectangular voltage pulses. The combination of lower amplitude HV pulses with a base direct current voltage, as compared with HV pulses only, allows some decrease in likelihood of a high voltage break down and a decrease in the interference electromagnetic signals emitted by the pulse generator into the lab environment.

An advantage of using a base direct current voltage is that the embodiment can be used with a pulse voltage supplier that supplies pulses with lower voltage. Such a voltage supplier is less expensive, but yet voltage pulses with the desired operating voltage may be predictably produced. The base direct current voltage is selected such that the total output voltage at the peak of a voltage pulse is the desired operating voltage for the individual treatment. The base direct current voltage is also chosen in consideration of the fact that only a negligible current should flow through the x-ray emitter 101 between any two voltage pulses. The direct current voltage is selected to be lower than the operating voltage. When the direct current voltage alone is applied, the emitter current may be negligibly low, for example, less than 0.5 $\mu$A, and does not contribute significantly to the irradiation of the tissue or to the thermal load of the catheter. For example the base direct current voltage may be selected such that the current flowing through the x-ray emitter 101 between two voltage pulses is less than 10% of the current flowing at the peak of a voltage pulse.

If the electrical current between the pulses is negligibly low, the electrical charge passed over one pulse, multiplied by the repetition rate, amounts to the average emitter current, which defines the average irradiation rate of the tissue. Because the electrical charge in any pulse is stabilized, and the repetition rate is assumed constant, the average current and the irradiation rate associated with it, is also stable. To provide a uniform irradiation, the speed of movement of the catheter along the vessel, in this case, can be kept constant during the procedure.

In the alternative, the rate of movement of the catheter can be controlled by the accumulated electrical charge in a predetermined number of pulses passed though the emitter. This method is preferred, as it does not depend on the static or dynamic errors of the electrical charge cut off and is therefore more precise.

In another implementation, the high voltage pulses have a fixed duration and a constant repetition rate. To provide a uniform irradiation along the vessel, in this case, the catheter movement rate is determined by the measured amount of electrical charge passed through the emitter over a number of fixed duration pulses. In this simplified version of the invention, the instability of the I–V characteristics does not affect the uniformity of the irradiation, only its duration. The drawback of this version is that the irradiation dose rate and the thermal load on the catheter to some extent depend on the instabilities of the I–V characteristics.

Preferably, the use of a high voltage pulse is practiced if the cold cathode has the ability to emit relatively high instant currents in comparison with direct current operations. To achieve an average current in the range of 30 to 50 $\mu A$, a pulse mode cold cathode should emit 5 to 10 times as high a current during a voltage pulse. A diamond coated cathode may allow that level of emission currents, as described in U.S. patent application Ser. No. 08/806,244.

When voltage is supplied to the x-ray emitter and x-ray radiation is emitted, heat will develop in the x-ray emitter as is well known. From the theory of heat transfer it is known that the temperature of a body, such as the x-ray emitter, may change significantly if it is heated during a time close to or higher than the time of thermal relaxation. To avoid unnecessary heating of the x-ray emitter, the duration of the pulse should be 2–5 times lower than the thermal relaxation time. As a result, the cooling time, i.e. the time between the pulses, should be 2–5 times higher than the thermal relaxation time.

A thermal analysis of the x-ray emitters of this invention shows that the time of relaxation is about 100–150 ms. Acceptable periodic voltage pulses may, for example, have a 50 ms pulse and a 200 ms cooling time, making the period of the pulses 250 ms. In one embodiment, the duty cycle, i.e. the ratio of the pulse to the period, is 20%. For other embodiments of the invention, duty cycles ranging from about 5% to 50%, or 10% to 30% may be used. The thermal relaxation time of a particular x-ray emitter configuration may be experimentally or theoretically determined.

Figure 2:
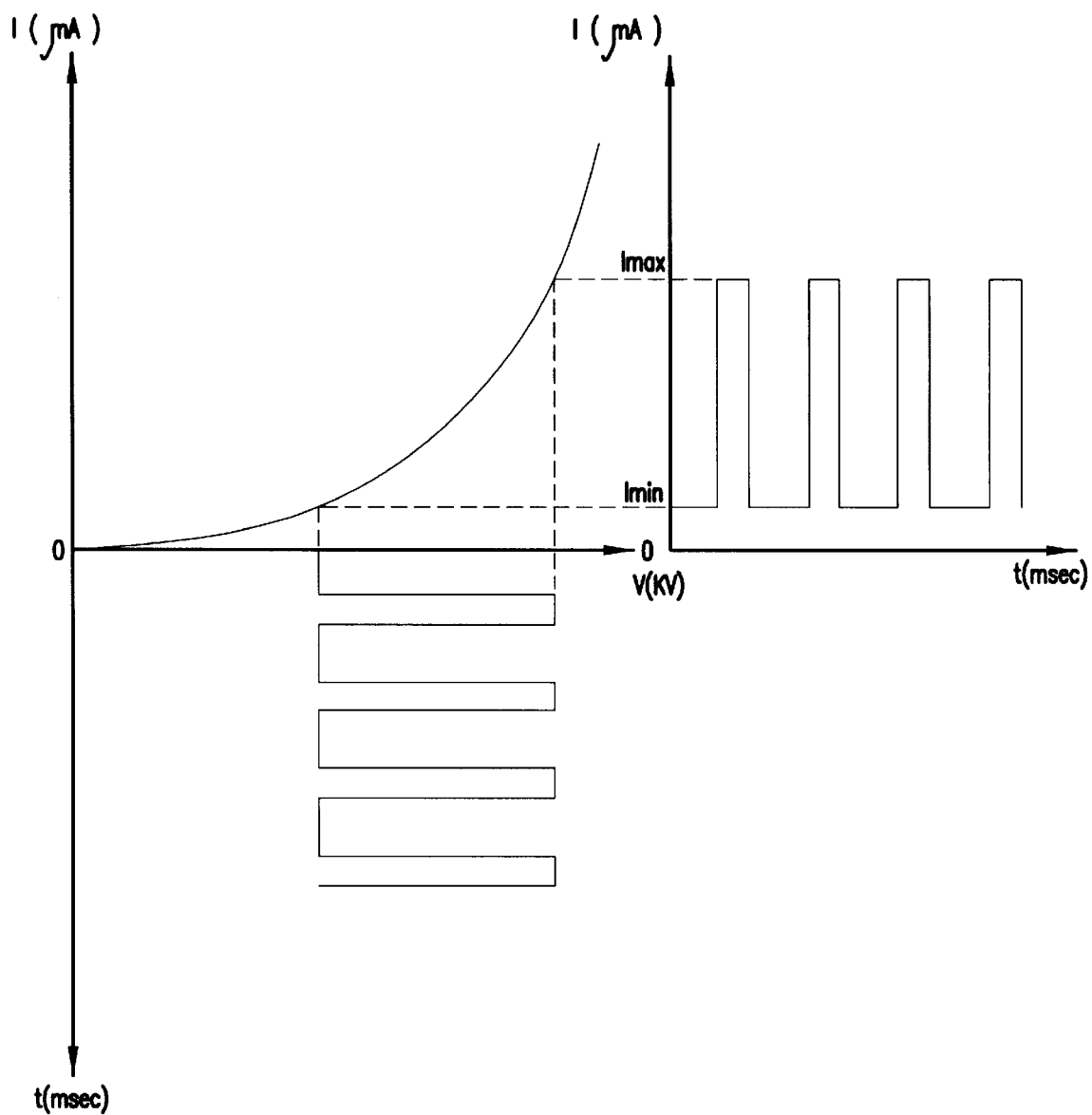
FIG. 2 is a current-voltage-time diagram, schematically showing the I–V characteristics of an x-ray emitter, an exemplary applied voltage as a function of time, and a current-time diagram, and the current through the x-ray emitter resulting from the exemplary applied voltage.

The above may be further understood by referring to FIG. 2 which schematically illustrate the current, voltage and time characteristics of the x-ray emitter. In FIG. 2, the applied voltage is illustrated as a function of time in the lower half of the diagram. The individual voltage pulses are shown, separated by cooling times as described above. As is well-known, an actual voltage pulse can only approximate the perfect rectangles shown in FIG. 1, and will have a shape somewhat different from a rectangle if measured with an oscilloscope. It is noted that a base direct current voltage is applied together with the pulses in the shown example. As a result, the voltage does not reach zero between pulses.

The I–V characteristics of an x-ray emitter is shown in the upper half of the diagram in FIG. 2. As described above, the anode current is a very steep function of the applied voltage. At the peak of a pulse, the current reaches a high current $I_{max}$, and between the pulses the current remains at a low current $I_{min}$. As noted above, the low current $I_{min}$ is preferably lower than the high current $I_{max}$ such that the low current $I_{min}$ does not contribute significantly to the delivered dose of radiation. The variation in the current due to the voltage pulses is illustrated in the upper right portion of FIG. 2. In accordance with FIG. 2, it can be seen that the current varies between $I_{min}$ and $I_{max}$ as a function of time.

Optionally, the apparatus 100 may comprise a voltage sensor 115. Well-known voltage sensors may be used with this embodiment. The voltage sensor is connected to the pulse voltage source 105 and may be connected to a current sensor 111.

The apparatus 100 may further comprise a control circuit 109 connected to the pulse voltage source 105. The control circuit 109 may comprise different configurations of circuit boards, components, input and output devices depending on the particular use of the invention. The control circuit 109 may, for example, be used to run a basic algorithm to control the components of the apparatus 100. For these purposes, the control circuit 109 may optionally be connected to devices such as a catheter pullback assembly 117, the voltage sensor 115, the current sensor 111, and the current integrator 113. For purposes of sharing measurements between the various components of the apparatus, there may be an electric or digital connection from the components to the control circuit. For other purposes, such as controlling the movement of the x-ray emitter via the catheter pullback assembly, there may be a mechanical connection, such as an actuator cable to the control circuit. The operation of the control circuit may be further understood by the following description of the use of the embodiment.

In using the embodiment of the invention, an x-ray emitter 101 is positioned in a passage inside the patient's body. The emitter and cable are placed into a body passage using well-known methods that may employ an incision and a blood vessel expander. The x-ray emitter is then positioned near a particular treatment site that is to be radiated. For example, the x-ray emitter 101 may be positioned distal to the treatment area, such that it may be successively withdrawn during the treatment to deliver radiation to the entire length of the treatment area. For example, the x-ray emitter 101 may be delivered by connecting the x-ray emitter to a cable 103, and advancing the cable 103 through a sheath 107 that has been introduced in the passage. Furthermore, the sheath may be advanced in the passage using a guide wire (not shown), by first introducing the guide wire in the passage, and then advancing the sheath 107 along the guide wire into the passage.

The cable 103 may optionally be connected to a carriage of the catheter pullback assembly 117. The sheath 107 may then be mounted on the body of the pullback assembly. By moving the carriage along the body of the catheter pullback assembly 117, the cable 103 may be actuated within the sheath 107. For example, the cable 103 may be retracted in the sheath 107 by pulling the carriage back on the body of the catheter pullback assembly 117. There may be markings on the body of the catheter pullback assembly 117 for indicating how far the cable 103 has been advanced in the sheath 107. The particular treatment parameters for the patient may be entered into the control circuit 109. For example, the operating voltage that is proportional to penetration depth of the radiation, the length of the treatment area, and the desired delivery dose, that depends on the surrounding tissue and the medical condition to be treated, may be entered as treatment parameters.

The dosage of x-ray radiation to be applied to the interior of a body will generally be within the scope of the attending physician's judgment, and will be based on individual conditions, such as the severity of damage that has occurred at the site to be treated and the particular patient. For example, in order to treat the early stages Barrett's esophagus, only the first layer of cells may need to be irradiated. If Barrett's esophagus has progressed to a cancerous state, the amount of radiation delivered will typically increase.

According to the present invention, x-ray radiation is applied as a total dosage and as a site specific dosage according to the accepted, known regiment for x-ray radiation of damaged tissue of the kind under consideration. For example, for restenosis, x-ray radiation in the range of 10 to 50 Grays may be applied to an area of the interior of a passage during treatment, for example, to prevent stenosis. Preferably, x-ray radiation in the range of 15 to 30 Grays may be applied to an interior body site. The treatment will be structured to last about 2 to 10 minutes, or, more preferably, 3 to 5 minutes. The x-ray emitter may be repositioned during the course of radiation treatment, depending on the length of the area requiring treatment.

When the x-ray emitter is in its initial position, and the treatment parameters have been entered, the treatment begins. Voltage pulses are supplied by the pulse voltage source 105 to the x-ray emitter 101. The emitter emits x-ray radiation to the surrounding tissue. The current through the emitter is measured by the current sensor 111, and the current values may be integrated by the current integrator 113. When the desired delivery dose during a pulse has been reached, as measured indirectly by the current sensor and integrator, the control circuit 109 may cause the pulse voltage source to discontinue the pulse. The control circuit may cause the catheter pullback assembly 117 to move at a constant rate because each pulse is stabilized. The x-ray emitter may be moved by steps of about 0.1 to 3 mm. The treatment procedure above may be repeated until the entire treatment area has been treated.

In the alternative, an amount of dose delivered per unit of time may be calculated on an on-going basis using the current sensor. The speed of catheter movement will be inversely proportional to the rate of dose delivery.

It is to be understood, that even though numerous characteristics and advantages of the invention have been set forth in the foregoing description, together with the details of the structure and function of the invention, the disclosure is illustrative only, and changes may be made in detail, especially in matters of shape, size, and arrangement of the parts within the principles of the invention to the full extent indicated by the broad general meaning of the terms in which the appended claims are expressed.

What is claimed is:

1. A device for delivering x-ray radiation, the device, comprising:

an x-ray emitter including a field emission cathode;

a pulse voltage source for supplying voltage pulses to the x-ray emitter, the voltage pulses having a controllable duty cycle;

a current sensor for measuring current through the x-ray emitter; and a control apparatus, operatively connected to the current sensor and to the pulse voltage source, providing control of the average current through the emitter by adjusting the duty cycle of the voltage pulses.

2. The device of claim 1 wherein the field emission cathode is an ungated field emission cathode.

3. The device of claim 1 wherein the control apparatus controls the average current by controlling a duration of the voltage pulses to allow a predetermined amount of charge to pass through the x-ray emitter during each pulse.

4. The device of claim 1 wherein the control apparatus controls the average current by adjusting a duration of the off time between pulses to allow a predetermined amount of electric charge to pass through the emitter during each period of the voltage pulse.

5. The device of claim 1 further comprising a current integrator connected to the current sensor and to the control apparatus, for integrating instant current values over time to determine the accumulated charge.

6. The device of claim 1 wherein the control apparatus is configured to provide the voltage pulses where a period of the voltage pulses is at least 2–5 times less than a thermal relaxation time of an emitter.

7. The device of claim 1 wherein the repetition rate of the voltage pulses is selected in the range between 50 Hz and 2000 Hz.

8. The device of claim 1 wherein the pulse voltage source supplies rectangular voltage pulses added to a base direct current voltage.

9. A method of using a device for delivering x-ray radiation comprising:

positioning an x-ray emitter having a field emission cathode near an area to be irradiated;

supplying voltage pulses from a voltage source to the x-ray emitter, the voltage pulses having a controllable duty cycle;

measuring the current passing through the x-ray emitter; and controlling the average current through the x-ray emitter by adjusting the duty cycle of the pulses.

10. The method of claim 9 further comprising monitoring instant current values through the emitter and integrating instant current values over time to determine the accumulated charge.

11. The method of claim 9 wherein the step of controlling includes adjusting a duration of the voltage pulses based on an amount of charge that has passed through the emitter.

12. The method of claim 9 wherein the step of controlling includes adjusting the duration of an off time of the voltage pulses based on an amount of charge that has passed through the emitter.

13. The method of claim 9 wherein the voltage pulses are rectangular voltage pulses added to a base direct current voltage.

14. The method of claim 9 wherein the voltage pulses supplied to the x-ray emitter have a period of at least 2–5 times less than a thermal relaxation time of an emitter.

15. The method of claim 9 wherein the voltage pulses supplied to the x-ray emitter have a repetition rate of 50 to 2000 Hz.

16. The method of claim 9 wherein the field emission cathode is an ungated field emission cathode.

\* \* \* \* \*